United States Patent [19]
Abe

[11] Patent Number: 5,431,022
[45] Date of Patent: Jul. 11, 1995

[54] COOLING BAG

[75] Inventor: Tomematsu Abe, Numazu, Japan

[73] Assignee: Kabushiki Kaisha Nichiwa, Numazu, Japan

[21] Appl. No.: 221,067

[22] Filed: Mar. 31, 1994

[30] Foreign Application Priority Data

Oct. 5, 1993 [JP] Japan ............................ 5-060552 U

[51] Int. Cl.⁶ .................................................. F25D 5/00
[52] U.S. Cl. ......................................... 62/4; 62/457.9; 62/259.3
[58] Field of Search ................... 62/4, 371, 372, 457.1, 62/457.9, 529, 530, 259.3; 126/204, 263

[56] References Cited

U.S. PATENT DOCUMENTS

| | | | |
|---|---|---|---|
| 2,541,736 | 2/1951 | Alexander | 126/263 DD |
| 3,175,558 | 3/1965 | Caillouette et al. | 126/263 |
| 4,067,313 | 1/1978 | Donnelly | 126/263 |
| 4,780,117 | 10/1988 | Lahey et al. | 62/4 |
| 4,967,573 | 11/1990 | Wilhelm | 62/4 |

FOREIGN PATENT DOCUMENTS

| | | |
|---|---|---|
| 580807 | 1/1959 | Canada ........................ 62/4 |
| 58-187482 | 11/1983 | Japan . |
| 63-259365 | 10/1988 | Japan . |
| 1-230689 | 9/1989 | Japan . |

Primary Examiner—John M. Sollecito
Attorney, Agent, or Firm—Flynn, Thiel, Boutell & Tanis

[57] ABSTRACT

Endothermic reaction (dissolution) of endothermic material to be packed in a cooling bag is retarded to avoid a large temperature gradient which results in a meaningless intake of ambient heat quantity and an excessively low temperature condition, so as to keep an adequately cooled condition for a long period of time. Column-like or tablet-like endothermic materials are prepared from granular starting materials to decrease their specific surface area and solution velocity in water. The products, either as they are alone, together with water absorbing resins and/or their granular starting endothermic materials, or as a stored state in a perforated inner bag, are packed in a bag made of synthetic resin film.

10 Claims, 1 Drawing Sheet

COOLING BAG

BACKGROUND OF THE INVENTION

1. Field of The Invention

This invention relates to a cooling bag for use in either cooling a limited part of human body, foods and drinks, various chemicals, cosmetics, biomaterials and the like or keeping those cold, and more particularly to a cooling bag which can exhibit an adequate and long-lasting cooling action effectively for a whole period of service.

2. Prior Art

It is well known to use granular ammonium nitrate, urea, etc. as an endothermic material for a cooling bag because such kind of materials absorb a large quantity of heat when they are dissolved in water. Although they are outstanding endothermic material from view points of their superior heat absorption characteristics, easier handling properties, economical advantages and the like, they begin to dissolve in instantly when water is added hereto due to their high moisture absorption and solubility in water. Then, in a short period of time, all amount of the endothermic material packed in the cooling bag dissolves to form an aqueous solution (solubilities of ammonium nitrate in 100 g. of water at temperatures of 0° C. and 30° C. being 118.3 g. and 241.8 g., respectively), thereby the water poured in the cooling bag is rapidly cooled to a temperature of −2° C. to −10° C. Such an excessively cooled condition in the bag is gradually moderated with a rise in temperature caused by a heat transfer from an object to be cooled such as a limited part of human body as well as an inevitable heat penetration thereinto from ambient environment other than the object and is warmed to a temperature of 0° C., 5° C., 10° C., 20° C. and higher, until the cooling bag is of no use any longer. Accordingly, an adequately cooled condition available as an effective low temperature source lasts only for rather a short period of time after water is poured. Further, the endothermic material such as granular ammonium nitrate, etc. absorbs moisture in the atmosphere due to its high hygroscopic nature during its storage even under a sealed condition in a polyethylene bag. Particularly, when the endothermic material meets with a temperature of 32.5° C. repeatedly during storage, it tends to integratedly coagulate and solidify in the bag to form an undesirably blocked mass thereof, which might cause an aesthetic deterioration as a commodity.

In order to effectively utilize a large quantity of heat of solution generated by the endothermic material such as ammonium nitrate, etc. for a specific usage, it is desirable, as will be described below, to control the apparent solution velocity in water and keep a low temperature of 0° C. to 2° C. or higher, and more preferably a temperature as in refrigerators for a long period of time after water is poured. A low temperature source capable of keeping such a low temperature is useful for cooling or keeping cold a limited part of human body such as a region of feverish or bruised or where capillary vessels are broken by heavy sports, or convenient for preserving and delivering many kinds of products such as raw creamed cake.

SUMMARY OF THE INVENTION

It is an object of this invention to provide a cooling bag which can exhibit an adequate cooling action for a long period of time without the aforesaid excessively cooled condition caused by conventional ammonium nitrate and can be conveniently used without any deformated disadvantage caused by coagulation and solidification of the endothermic material.

The ammonium nitrate, etc. packed as an endothermic material in the cooling bag of this invention is prepared by melting granular ammonium nitrate, etc. as a starting material to form column-like or tablet-like products. While an endothermic product formed from a melt mixture of ammonium nitrate and urea exhibits an extremely high moisture absorption, they should be melted and formed independently. It is further apprehensive that the endothermic product thus independently prepared would absorb moisture and deteriorate depending on storage conditions such as humidity, temperature, storing period and the like as well as sealing conditions such as materials of which the cooling bag is made, and kinds and/or properties of sealing means including check valves, chucks, etc. and, consequently, a drying agent may be present together in such a case. Silica gel is a preferable drying agent which does not affect neither dissolution nor endothermic reaction of ammonium nitrate, urea, etc.

PREFERRED EMBODIMENT OF THE INVENTION

Figure 1:
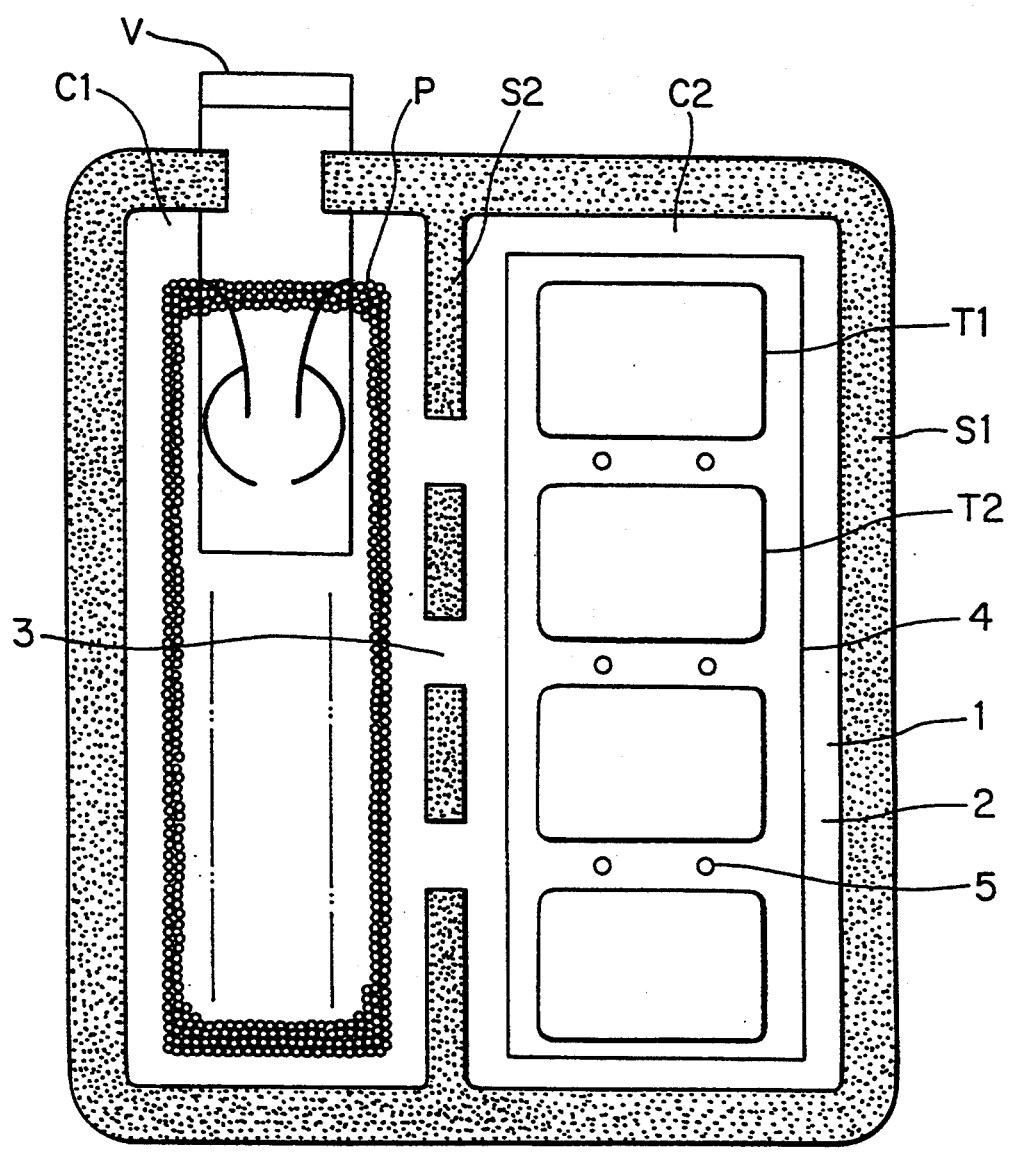
FIG. 1 is an illustrative view showing an example of the present cooling bag packed with melt formed column-like endothermic material in an inner bag and a starting granular endothermic material.

This invention will be described in the following example.

Commercially available granular ammonium nitrate and urea are subjected to a melt forming process independently to obtain column-like products (about 22 g/piece). Two sheets of polyethylene film 1 and 2 of the same shape and same size (15 cm×20 cm), each one surface of which being deposited with aluminum, are laid one on top of another, applied thereto heat seals S1 and S2 along all the periphery and almost in the center of the sheets at intervals, respectively, so as to leave a passage 3 on the line of the seal S2, and attached with a check valve V detailed description of which is seen in Applicant's U.S. Pat. No. 5,308,163 to one side thereof to make a bag. The bag is provided with compartments C1 and C2 communicating with each other through the passage 3, the aluminum deposition being faced outward and apart of the heat seal S1 along a part of the periphery being left open until the endothermic materials are packed. Then, packed into the compartment C1 is 25 g. of starting granular ammonium nitrate P. A polyethylene inner bag 4 having perforations 5 of 0.1 mm diameter, which bag holds both one piece of column-like ammonium nitrate product T1 and three pieces of column-like urea product T2 is packed in the compartment C2 to complete the cooling bag. In this embodiment a water absorbing resin has not been used.

The cooling bag thus completed exhibits the following properties when 60 ml of tap water at 25° C. is poured therein through the check valve V, then being allowed to stand under a condition of a room temperature at 25° C. and a humidity of 70% R.H.;

average lowest temperature around the surface region: 2.8° C.

(time required to reach the lowest temperature: 7.5 min.) and time capable of keeping the temperature below 15° C.: 90 min.

Although FIG. 1 shows a cooling bag of two compartments type, a third compartment (not shown) may be allocated symmetrically to the other half side of the compartment C1 for packing the melt formed products, etc., which would constitute a three compartments type.

As is clear from detailed description mentioned above, the apparent solution velocity of the endothermic material is decreased by compulsively delaying its dissolution into a complete solution to avoid unnecessarily low temperature conditions, which might be harmful even if such conditions occur and last only for a short period of time, and accordingly the cooling bag capable of exhibiting an mildly averaged cooling ability for a long period of time can be provided by this invention. Further, the cooling bag of this invention is hardly deformed due to coagulation or solidification of the endothermic materials packed therein, because they are previously formed as solid column-like or tablet-like products.

As these column-like or tablet-like products have markedly smaller specific surface area, and accordingly smaller contact area with poured water, than that of starting granular ammonium nitrate, etc., the time required for the complete dissolution thereof into an aqueous solution in the cooling bag is several times as large as that of the starting granular materials. The excessively cold condition of the bag followed by addition of water, which is caused by above mentioned dissolution into a complete solution during a short period of time, is thus avoided. An excessively large difference in temperature between the cooling bag and an ambient environment thereof, which is unpleasant, harmful or unnecessary in case of applying the cooling bag to a limited part of human body or other subjects to be cooled, is successfully conquered. According to this invention, the heat of solution of ammonium nitrate, etc. is utilized without any thermal loss so that the cooling or cold keeping ability of the bag is averaged evenly, thereby a longer term cooling performance is attained. As the time required for the present product to reach the lowest temperature is about 10 minutes or so after water is poured, while that of the granular ammonium nitrate is around 5 minutes, the present column-like or tablet-like product may be used together with a small amount of such starting granular materials to attain quickly a low temperature condition in case of an emergency or if water to be poured is too warm to get a sufficient low temperature at the beginning stage.

According to this invention, the apparent solution velocity of the ammonium nitrate product, etc. prepared by the melt forming process exhibits a further decreased value when a water absorbing resin is added together and/or an inner bag is used. Well known water absorbing resins such as polyacrylic resins, for example, those of a Aqualic CAS type available from Nihon Shokubai Co., Ltd. yield a gel product when water is added. As a result, the mobility of a portion of low temperature water, a kind of cold water lump formed by dissolution of such heat absorbing materials in water, is considerably restricted because it takes a longer period of time to thoroughly spread the portion in question. If these resins are used practically in the cooling bag, it is possible to prevent inconvenient or unexpected accidents where, for example, a sealing means such as a check valve or chuck attached thereto is unworkably chilled leaving a deformed state due to a low temperature and happens to cause an incomplete sealing of water or a substantial leakage of water. Also, it is effective to add an appropriate thickening material in the present bag. The inner bag usable in this invention is made of synthetic resin film and have an opening at one side and an appropriate number of perforations on one of or each of surface, which may store the melt formed product therein and be disposed in the cooling bag as it is. The size and number of perforations may be determined in a range sufficient to control and at the same time to allow said cold water lump formed in the cooling bag to spread and mobilize to some extent.

The column-like or tablet-like product may also be prepared by compression forming process comprising adding a small amount of water to a starting granular mixture such as ammonium nitrate and urea at a weight ratio of 20 to 40:80 to 60, and solidifying the mixture under pressure. Although the rate of dissolution into a complete solution of thus prepared is slightly faster than that of the melt formed product and correspondingly the lowest temperature given by the former is lower than that of the latter, this product may also be used to accomplish the object of this invention.

What is claimed is:

1. A cooling bag for applying cold to an object, said cooling bag being light in weight due to the absence of water and capable of generating said cold for a predetermined period of time, said cooling bag comprising:
 a bag-like enclosure defining at least one compartment within the cooling bag;
 a cold generating endothermic material for producing an endothermic reaction upon contact with water and disposed within said compartment, said endothermic material formed as a tablet-like solid having a reduced specific surface area to reduce a reaction rate of said endothermic material when in contact with water; and
 a closable valve on said bag-like enclosure for permitting water to be supplied therethrough from outside said cooling bag into said compartment.

2. A cooling bag as claimed in claim 1 wherein said endothermic material is stored in a perforated inner bag disposed within said bag-like enclosure.

3. A cooling bag as claimed in claim 1 wherein said endothermic material is ammonium nitrate.

4. A cooling bag as claimed in claim 1 wherein said endothermic material is urea.

5. A cooling bag as claimed in claim 1 wherein said endothermic material is ammonium nitrate and urea.

6. A cooling bag as claimed in claim 1 wherein a quantity of loose granular endothermic starting material is provided within said compartment.

7. A cooling bag as claimed in claim 6 wherein said bag-like enclosure defines at least two of said compartments which communicate with each other by a small passage formed therebetween so as to permit flow of water therebetween, said tablet-like solid being in one said compartment, and said valve is a one-way check valve communicating directly with the other said compartment.

8. A cooling bag as claimed in claim 7 wherein said endothermic material is packed in an inner bag disposed in said one compartment and said granular starting material is packed in said other compartment, said other compartment being in communication with said closable valve for receiving water therein to provide an initial endothermic reaction, said inner bag having perforations to receive water from said one compartment therethrough into said inner bag and provide a defined flow of water therein to regulate a reaction rate of the water with the tablet-shaped solid of endothermic material.

9. A cooling bag for applying cold to an object, said cooling bag being light in weight due to the absence of water and capable of generating said cold for a predetermined period of time, said cooling bag comprising:
   a bag-like enclosure defining at least first and second compartments, said first and second compartments communicating one with the other by at least one small passage formed therebetween;
   a closable valve on said bag-like enclosure in communication with only said first compartment for receiving water therethrough into said first compartment;
   a granular endothermic starting material disposed within said first compartment to provide an initial endothermic reaction upon contact with water received therein through said closable valve; and
   a tablet-like member of endothermic material disposed within said second compartment for producing an endothermic reaction upon contact with water received from said first compartment through said passage, said tablet-like member of endothermic material forming a solid of reduced surface area to regulate the reaction rate thereof when in contact with water.

10. A cooling bag as claimed in claim 9 wherein said tablet-like member of endothermic material is stored in a perforated inner bag disposed within said second compartment, said inner bag having perforations which regulate flow of water into said inner bag to further regulate the reaction rate of said water with said tablet-like member of endothermic material.

* * * * *